US012156757B2

(12) United States Patent
Kinoshita (10) Patent No.: US 12,156,757 B2
(45) Date of Patent: Dec. 3, 2024

(54) ROTATION MECHANISM FOR X-RAY INSPECTION APPARATUS, X-RAY INSPECTION APPARATUS, AND METHOD OF ADJUSTING ROTATION MECHANISM FOR X-RAY INSPECTION APPARATUS

(71) Applicant: JED CO., LTD, Azumino (JP)

(72) Inventor: Osamu Kinoshita, Azumino (JP)

(73) Assignee: JED Co., Ltd. (JP)

( * ) Notice: Subject to any disclaimer, the term of this patent is extended or adjusted under 35 U.S.C. 154(b) by 264 days.

(21) Appl. No.: 17/911,795

(22) PCT Filed: Oct. 7, 2021

(86) PCT No.: PCT/JP2021/037107
§ 371 (c)(1),
(2) Date: Sep. 15, 2022

(87) PCT Pub. No.: WO2022/113533
PCT Pub. Date: Jun. 2, 2022

(65) Prior Publication Data
US 2023/0119131 A1    Apr. 20, 2023

(30) Foreign Application Priority Data
Nov. 26, 2020 (JP) ................. 2020-195754

(51) Int. Cl.
*A61B 6/00* (2024.01)
(52) U.S. Cl.
CPC .......... *A61B 6/4452* (2013.01); *A61B 6/4476* (2013.01)

(58) Field of Classification Search
CPC ...... F16C 35/077; F16C 35/067; F16C 23/06; F16C 23/10; F16C 35/063; F16C 2226/60;
(Continued)

(56) References Cited

U.S. PATENT DOCUMENTS 4,854,750 A * 8/1989 Lavin ................ F16C 19/08
384/500
6,459,759 B1   10/2002 Tominaga
(Continued)

FOREIGN PATENT DOCUMENTS

JP    2000-266694 A    9/2000
JP    2010-230053 A   10/2010
(Continued)

OTHER PUBLICATIONS

International Search Report (English and Language) issued in PCT/JP2021/037107, mailed Dec. 21, 2021; ISA/JP (6 pages).

*Primary Examiner* — Irakli Kiknadze
(74) *Attorney, Agent, or Firm* — Harness, Dickey & Pierce, P.L.C.

(57) ABSTRACT

In the rotation mechanism for an X-ray inspection apparatus, a plurality of adjustment members configured to adjust the shape of an outer race of a bearing by deforming the outer race are arranged in a circumferential direction of the bearing. The adjustment members are movable relative to an adjustment member holder in a diameter direction of the bearing and contactable with an outer circumferential surface of the outer race. A gap S configured to allow deformation of the outer race is formed between the outer circumferential surface of the outer race and the adjustment member holder in the diameter direction of the bearing.

7 Claims, 6 Drawing Sheets

(58) Field of Classification Search
CPC .... F16C 2300/14; F16C 33/60; F16C 19/362; F16C 2316/10; F16C 33/122; F16C 33/545; F16C 25/083; F16C 2361/61; F16C 33/585; F16C 19/386; F16C 33/581; F16C 19/163; F16C 33/62; F16C 25/06; F16C 19/183; F16C 19/36; F16C 19/38; F16C 35/12; F16C 33/586; F16C 2370/00; F16C 2223/70; F16C 2223/30; F16C 19/166; F16C 41/00; F16C 19/04; F16C 11/10; F16C 19/06; F16C 27/045; F16C 2226/62; F16C 2360/23; G01N 23/043; G01N 23/046; G01N 33/442; G01N 2223/645; G01N 2223/419; G01N 2223/623; G01N 2223/406; G01N 2223/615; G01N 33/386; G01N 23/044; A61B 6/4476; A61B 6/4452; G01B 15/00; G01B 21/04; F16H 2057/085
USPC .................................. 378/20, 197, 208, 209
See application file for complete search history.

(56) References Cited

U.S. PATENT DOCUMENTS

| | | | |
|---|---|---|---|
| 6,682,226 | B2 | 1/2004 | Kotzalas et al. |
| 7,373,676 | B2 * | 5/2008 | Markovic ............ A61N 5/1049 5/601 |
| 10,760,614 | B2 * | 9/2020 | Taguchi ................ F16C 27/045 |
| 2015/0003578 | A1 | 1/2015 | Kim et al. |

FOREIGN PATENT DOCUMENTS

| | | |
|---|---|---|
| JP | 2012-112790 A | 6/2012 |
| JP | 2012-172774 A | 9/2012 |
| JP | 2015-502555 A | 1/2015 |
| JP | 2019-60808 A | 4/2019 |

* cited by examiner

ROTATION MECHANISM FOR X-RAY INSPECTION APPARATUS, X-RAY INSPECTION APPARATUS, AND METHOD OF ADJUSTING ROTATION MECHANISM FOR X-RAY INSPECTION APPARATUS

CROSS REFERENCE TO RELATED APPLICATIONS

This application is a U.S. National Phase Application under 35 U.S.C. 371 of International Application No. PCT/JP2021/037107, filed on Oct. 7, 2021, which claims priority to Japanese Patent Application No. 2020-195754, filed on Nov. 26, 2020. The entire disclosures of the above applications are expressly incorporated by reference herein.

BACKGROUND

Technical Field

The present invention relates to a rotation mechanism for an X-ray inspection apparatus used in an X-ray inspection apparatus for nondestructively inspecting an object to be inspected, such as an industrial product. The present invention also relates to an X-ray inspection apparatus including this rotation mechanism for an X-ray inspection apparatus. Furthermore, the present invention relates to a method of adjusting a rotation mechanism for an X-ray inspection apparatus used in an X-ray inspection apparatus.

Related Art

A conventional inspection apparatus has been known for inspecting a board having a flat plate shape (for example, see Japanese Patent Application Laid-open No. 2019-60808). An inspection apparatus disclosed in Japanese Patent Application Laid-open No. 2019-60808 includes a radiation generator emitting radiation, such as X-rays, toward a board, a board holder holding the board, and a detector taking an image of the board. The board is held by the board holder, for example, with the thickness direction of the board coinciding with the vertical direction. The radiation generator is disposed above the board holder, and the detector is disposed below the board holder. The inspection apparatus disclosed in Japanese Patent Application Laid-open No. 2019-60808 also includes a board holder driver. The board holder driver includes a horizontal movement mechanism moving the board holder horizontally and a rotation mechanism rotating the board holder.

Figure 5:
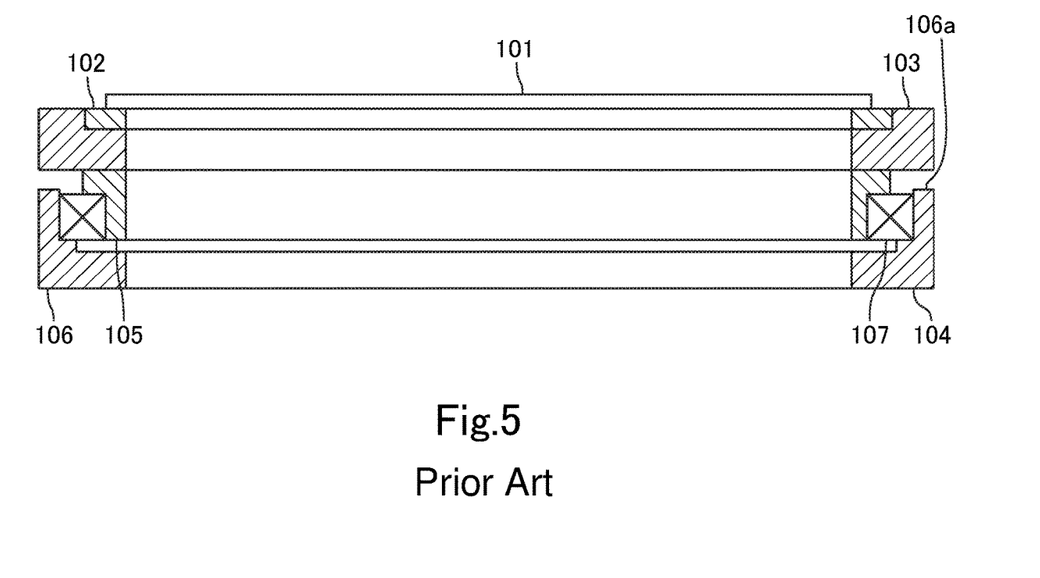
FIG. 5 is an explanatory diagram of a configuration of a rotation mechanism for an inspection apparatus according to a conventional art.

Furthermore, as a conventional inspection apparatus for inspecting a flat plate shaped board like the inspection apparatus disclosed in Japanese Patent Application Laid-open No. 2019-60808, for example, an inspection apparatus, as illustrated in FIG. 5, is also used which includes a board holder 102 holding a board 101, an XY table 103 moving the board holder 102 in two horizontal directions, and a rotation mechanism 104 on which the XY table 103 is mounted. In this inspection apparatus, a radiation generator is disposed above the board holder 102, and a detector is disposed below the rotation mechanism 104.

The rotation mechanism 104 rotates the XY table 103 using the vertical direction as a rotation axis direction. In the board holder 102, the XY table 103, and the rotation mechanism 104, through holes that pass therethrough vertically are formed, and radiation emitted from the radiation generator passes through these through holes. The rotation mechanism 104 includes, for example, a table 105 to which the XY table 103 is fixed, a table holding member 106 rotatably holding the table 105, and a driving mechanism rotating the table 105.

Between the table 105 and the table holding member 106, a rolling bearing 107 having a relatively large inner diameter is disposed. The rolling bearing 107 has an outer race fixed to the table holding member 106 and an inner race fixed to the table 105. On the table holding member 106, for example, a cylindrical outer race fixer 106a is formed, and the outer race of the rolling bearing 107 is press-fitted and fixed on the inner circumferential side of the outer race fixer 106a. In this case, the outer race of the rolling bearing 107 can be fixed to the table holding member 106 with high accuracy.

As illustrated in FIG. 5, when the outer race of the rolling bearing 107 is press-fitted and fixed on the inner circumferential side of the outer race fixer 106a, the outer race of the rolling bearing 107 may deform depending on the shape of the inner circumferential surface of the outer race fixer 106a. If the outer race of the rolling bearing 107 deforms, the rotation loci of the inner race of the rolling bearing 107 and the table 105 rotating along the outer race of the rolling bearing 107 may greatly differ from a perfect circle. That is, if the outer race of the rolling bearing 107 deforms, the rotation locus of the board 101 may greatly differ from a perfect circle. Furthermore, if the rotation locus of the board 101 greatly differs from a perfect circle, a reconstructed image reconstructed on the basis of a plurality of images of the board 101 acquired by the detector may have reduced accuracy.

Therefore, an object of the present invention is to provide a rotation mechanism for an X-ray inspection apparatus that can bring the rotation locus of a rotating object to be inspected near to a perfect circle in the rotation mechanism for an X-ray inspection apparatus used in an X-ray inspection apparatus. Furthermore, an object of the present invention is to provide an X-ray inspection apparatus including this rotation mechanism for an X-ray inspection apparatus. Moreover, an object of the present invention is to provide a method of adjusting a rotation mechanism for an X-ray inspection apparatus that can bring the rotation locus of a rotating object to be inspected near to a perfect circle in the method of adjusting a rotation mechanism for an X-ray inspection apparatus used in an X-ray inspection apparatus.

SUMMARY

To solve the above problems, a rotation mechanism for an X-ray inspection apparatus according to the present invention, used in an X-ray inspection apparatus including an X-ray generator and an X-ray detector disposed with an object to be inspected placed between the X-ray detector and the X-ray generator, includes: a table; a table holding member rotatably holding the table; a rolling bearing including an inner race and an outer race, the inner race having a ring shape and being fixed to either one of the table and the table holding member, the outer race having a ring shape and being fixed to another of the table and the table holding member; and three or more adjustment members configured to adjust a shape of the outer race by deforming the outer race. The adjustment members are arranged in a circumferential direction of the rolling bearing. The table or the table holding member to which the outer race is fixed includes an adjustment member holder movably holding the adjustment members, the adjustment member holder being disposed on an outer circumferential side of the outer race. The adjustment members are movable relative to the adjustment member holder in a diameter direction of the rolling bearing and are contactable with an outer circumferential surface of the outer race. A gap configured to allow deformation of the outer race is formed between the outer circumferential surface of the outer race and the adjustment member holder in the diameter direction of the rolling bearing. According to the present invention, the outer race is fixed, for example, to the table holding member.

In the rotation mechanism for the X-ray inspection apparatus according to the present invention, the three or more adjustment members configured to adjust the shape of the outer race by deforming the outer race are arranged in the circumferential direction of the rolling bearing. Furthermore, according to the present invention, the adjustment members are movable relative to the adjustment member holder in the diameter direction of the rolling bearing and contactable with the outer circumferential surface of the outer race. Moreover, according to the present invention, the gap configured to allow deformation of the outer race is formed between the outer circumferential surface of the outer race and the adjustment member holder in the diameter direction of the rolling bearing. Thus, according to the present invention, with the shape of the outer race adjusted using the adjustment members so that the rotation locus of the object to be inspected rotated by the rotation mechanism for an X-ray inspection apparatus near to a perfect circle, the outer race can be fixed to the table or the table holding member. Therefore, according to the present invention, the rotation locus of the object to be inspected rotated by the rotation mechanism for an X-ray inspection apparatus can be brought near to a perfect circle.

According to the present invention, the adjustment members are preferably adjusting screws composed of screws, and threaded holes are preferably formed in the adjustment member holder, the threaded holes engaging with the adjusting screws and passing through the adjustment member holder in the diameter direction of the rolling bearing. With this configuration, the outer race can be deformed in accordance with the amount of rotation of the adjusting screws. Thus, the shape of the outer race can be readily adjusted.

According to the present invention, the rotation mechanism for an X-ray inspection apparatus preferably includes looseness preventing screws configured to prevent looseness of the adjusting screws, and the looseness preventing screws preferably engage with the threaded holes from outside the adjusting screws in the diameter direction of the rolling bearing. With this configuration, engagement of the looseness preventing screw with the threaded hole engaging with the adjusting screws can prevent looseness of the adjusting screws. Thus, a simple configuration can prevent looseness of the adjusting screws.

According to the present invention, the rolling bearing is, for example, a cross roller bearing. In this case, the rotation accuracy of the object to be inspected rotated by the rotation mechanism for an X-ray inspection apparatus can be improved. Furthermore, according to the present invention, for example, an X-ray inspection apparatus includes the above-described rotation mechanism for an X-ray inspection apparatus.

Furthermore, to solve the above problems, a method of adjusting a rotation mechanism for an X-ray inspection apparatus according to the present invention, used in an X-ray inspection apparatus including an X-ray generator and an X-ray detector disposed with an object to be inspected placed between the X-ray detector and the X-ray generator, the rotation mechanism including a table, a table holding member rotatably holding the table, and a rolling bearing including an inner race and an outer race, the inner race having a ring shape and being fixed to either one of the table and the table holding member, the outer race having a ring shape and being fixed to another of the table and the table holding member, includes: fixing the outer race to the table or the table holding member with a shape of the outer race adjusted by bringing a plurality of adjustment members into contact with an outer circumferential surface of the outer race, the adjustment members being configured to adjust the shape of the outer race by deforming the outer race, the adjustment members being arranged in a circumferential direction of the rolling bearing.

In the method of adjusting the rotation mechanism for an X-ray inspection apparatus according to the present invention, with the shape of the outer race adjusted by bringing the adjustment members that are configured to adjust the shape of the outer race by deforming the outer race and that are arranged in the circumferential direction of the rolling bearing into contact with the outer circumferential surface of the outer race, the outer race is fixed to the table or the table holding member. Thus, according to the present invention, with the shape of the outer race adjusted using the adjustment members so that the rotation locus of the object to be inspected rotated by the rotation mechanism for an X-ray inspection apparatus near to a perfect circle, the outer race can be fixed to the table or the table holding member. Therefore, through adjustment by the method of adjusting the rotation mechanism for an X-ray inspection apparatus according to the present invention, the rotation locus of the object to be inspected rotated by the rotation mechanism for an X-ray inspection apparatus can be brought near to a perfect circle.

Advantageous Effects of Invention

As described above, the rotation mechanism for an X-ray inspection apparatus according to the present invention can bring the rotation locus of a rotating object to be inspected near to a perfect circle. Furthermore, through adjustment by the method of adjusting the rotation mechanism for an X-ray inspection apparatus according to the present invention, the rotation locus of a rotating object to be inspected can be brought near to a perfect circle.

DETAILED DESCRIPTION

Embodiments of the present invention will be described below with reference to the drawings.

(Configuration of X-Ray Inspection Apparatus)

Figure 1:
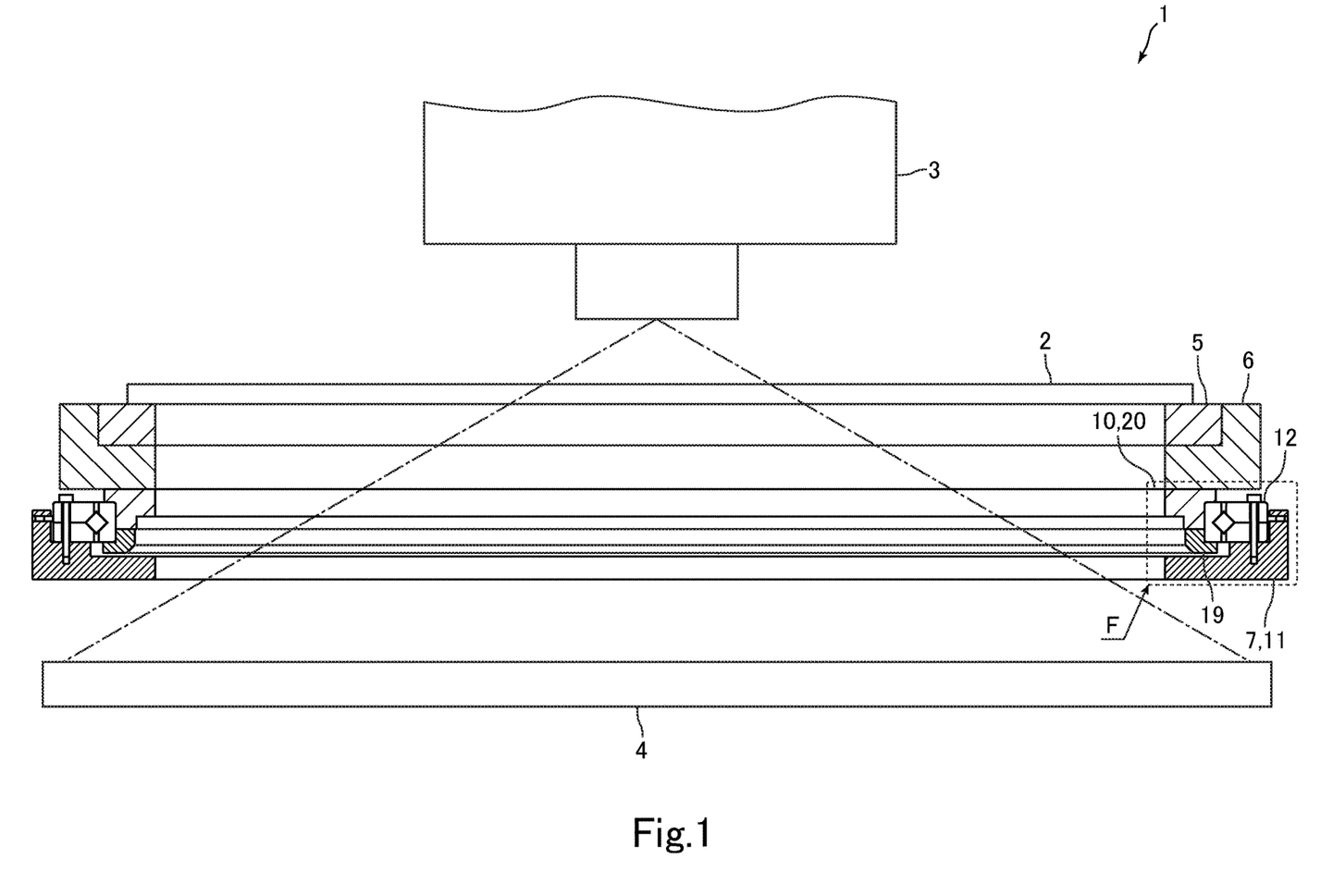
FIG. 1 is an explanatory diagram of a schematic configuration of an X-ray inspection apparatus according to an embodiment of the present invention.

FIG. 1 is an explanatory diagram of a schematic configuration of an X-ray inspection apparatus 1 according to an embodiment of the present invention.

The X-ray inspection apparatus 1 of this embodiment is an apparatus for nondestructively inspecting an object 2 to be inspected, such as an industrial product. The object 2 to be inspected of this embodiment is a board (circuit board), such as a glass epoxy board shaped into a flat plate. Thus, hereinafter, the object 2 to be inspected is referred to as a "board 2". On the board 2, an electronic component, such as an IC chip, is mounted. The X-ray inspection apparatus 1 inspects a joint between the board 2 and the electronic component through so-called oblique CT. Inspection with the X-ray inspection apparatus 1 thus requires high inspection accuracy, for example, in micron units.

The X-ray inspection apparatus 1 includes an X-ray generator 3 that emits X-rays toward the board 2, an X-ray detector 4 that is disposed with the board 2 placed between the X-ray detector 4 and the X-ray generator 3 and acquires an X-ray image of the board 2, a placing stand 5 on which the board 2 is placed, an XY table 6 to which the placing stand 5 is attached, and a rotation mechanism (rotation mechanism for an X-ray inspection apparatus) 7 on which the XY table 6 is mounted. The board 2 is placed on the placing stand 5 with the thickness direction of the board 2 coinciding with the vertical direction.

The X-ray generator 3 emits conical X-rays toward the board 2. The X-ray detector 4 is a two-dimensional X-ray detector (area sensor). The X-ray detector 4 is disposed with a light-receiving surface of the X-ray detector 4 facing the X-ray generator 3, and a fluoroscopic image of the board 2 is projected on the X-ray detector 4. The X-ray generator 3 and the X-ray detector 4 are disposed with the board 2 placed therebetween in the vertical direction. A portion of the board 2 is placed between the X-ray generator 3 and the X-ray detector 4. The placing stand 5 is detachably attached to an upper end portion of the XY table 6. The XY table 6 is attached to an upper end of the rotation mechanism 7 and disposed above the rotation mechanism 7. The X-ray generator 3 is disposed above the board 2. The X-ray detector 4 is disposed below the rotation mechanism 7.

The XY table 6 includes a first movable table to which the placing stand 5 is attached, a first table driving mechanism moving the first movable table in an X direction orthogonal to the vertical direction, a second movable table on which the first movable table and the first table driving mechanism are mounted, a second table driving mechanism moving the second movable table in a Y direction orthogonal to the vertical direction and the X direction, and a stationary table on which the second movable table and the second table driving mechanism are mounted. In the placing stand 5, the first movable table, the second movable table, and the stationary table, through holes are formed for transmitting X-rays emitted from the X-ray generator 3.

The rotation mechanism 7 includes a table 10 to which the stationary table of the XY table 6 is attached, a table holding member 11 rotatably holding the table 10, and a rolling bearing 12 disposed between the table 10 and the table holding member 11. The rotation mechanism 7 rotates the XY table 6 using the vertical direction as a rotation axis direction. That is, the rotation mechanism 7 rotates the board 2 placed on the placing stand 5 using the vertical direction as the rotation axis direction. A specific configuration of the rotation mechanism 7 will be described later.

When the X-ray inspection apparatus 1 inspects the board 2, the X-ray generator 3 emits X-rays toward the board 2 rotated by the rotation mechanism 7 at a constant speed. The X-ray detector 4 sequentially acquires a plurality of two-dimensional X-ray images depicting the fluoroscopic image of the board 2. Specifically, the X-ray detector 4 continuously acquires the X-ray image every time the board 2 is rotated by a certain angle. The X-ray images acquired by the X-ray detector 4 are captured into, for example, a personal computer (PC). The PC performs predetermined arithmetic processing to generate a CT image of the board 2 on the basis of the X-ray images. Note that, when the X-ray inspection apparatus 1 inspects the board 2, the X-ray detector 4 may sequentially acquire two-dimensional X-ray images depicting the fluoroscopic image of the board 2 while the table 10 is paused in positions obtained by equally dividing 360°.

(Configuration of Rotation Mechanism)

Figure 2A:
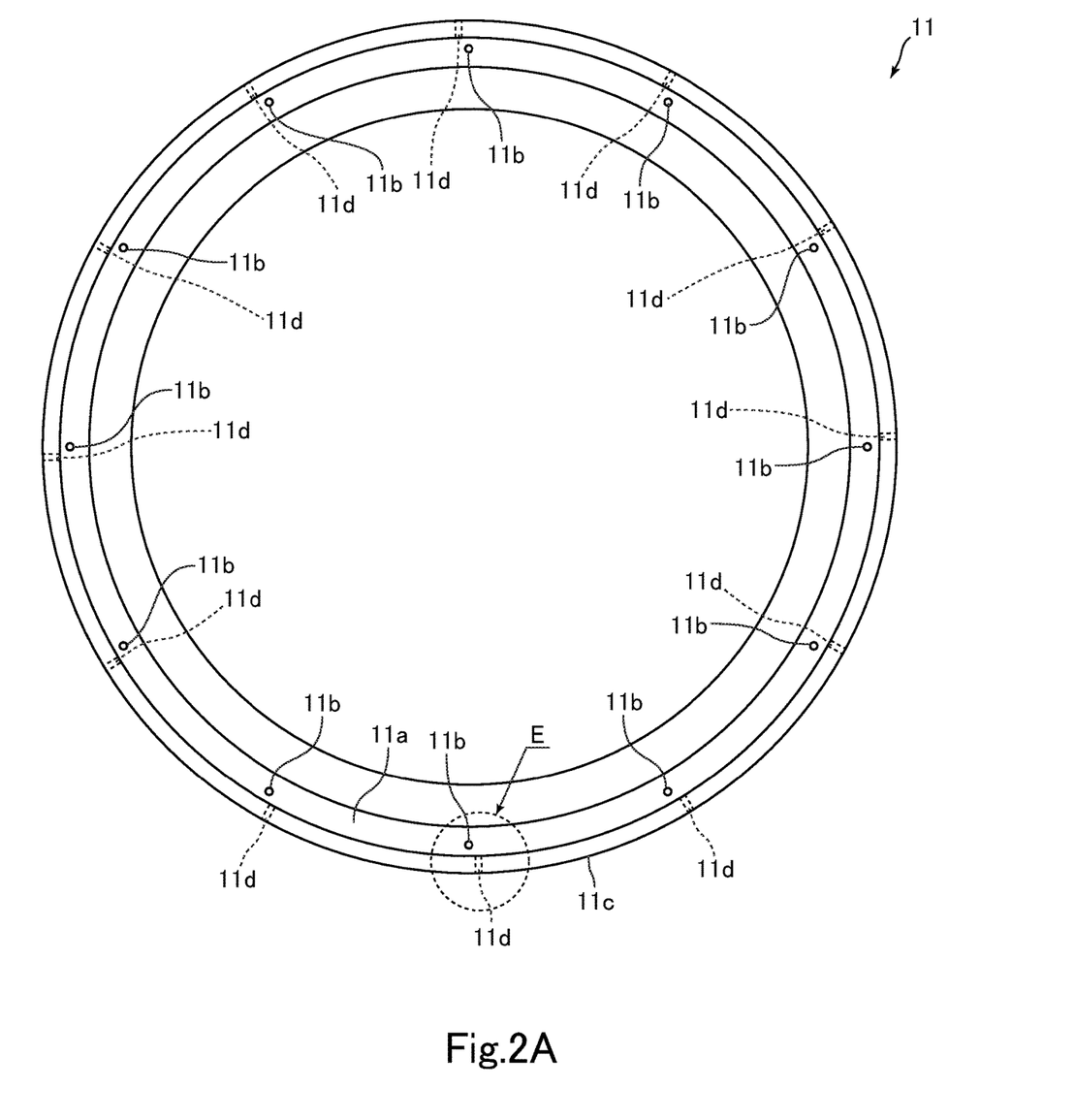
FIG. 2(A) is a plan view of a table holding member illustrated in FIG. 1.
Figure 2B:
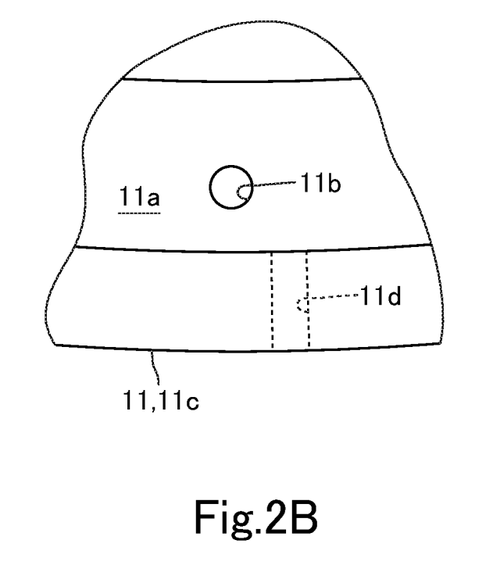
FIG. 2(B) is an enlarged view of a portion E in FIG. 2(A).
Figure 3:
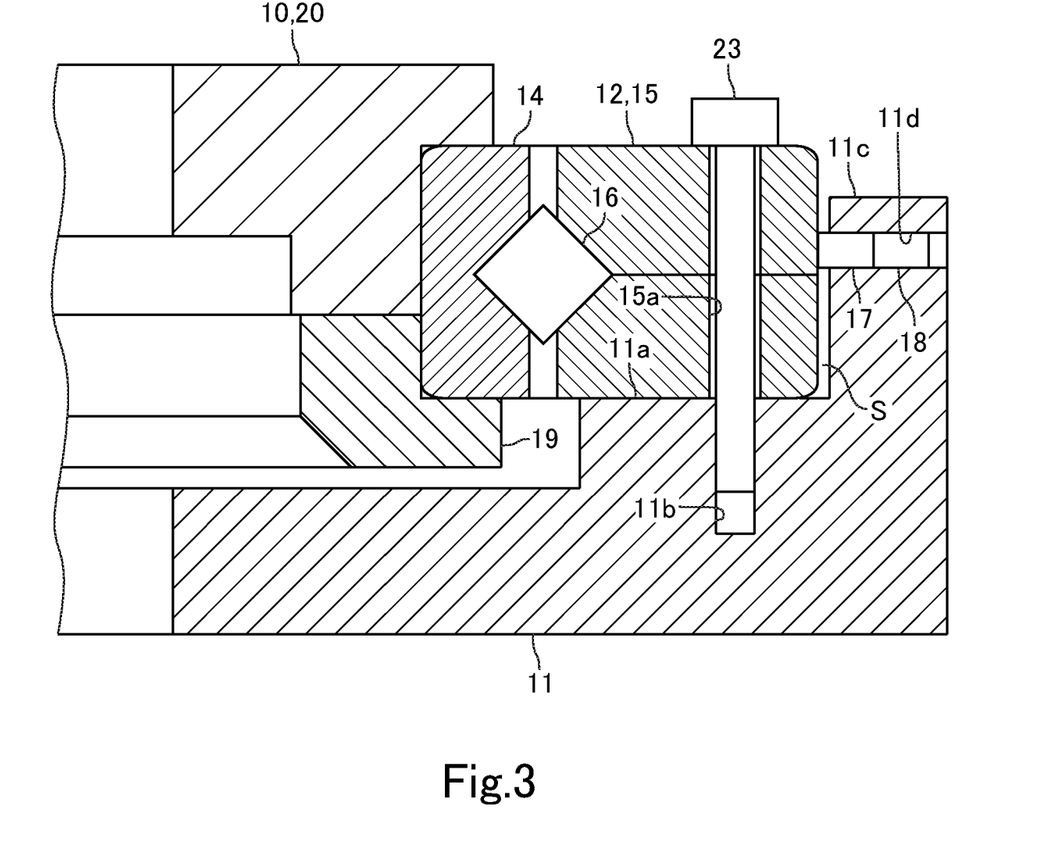
FIG. 3 is an enlarged view for describing a configuration of a portion F in FIG. 1.

FIG. 2(A) is a plan view of the table holding member 11 illustrated in FIG. 1, and FIG. 2(B) is an enlarged view of a portion E in FIG. 2(A). FIG. 3 is an enlarged view for describing a configuration of a portion F in FIG. 1.

The rotation mechanism 7 includes a driving mechanism (not illustrated) rotating the table 10 in addition to the table 10, the table holding member 11, and the rolling bearing 12 described above. The driving mechanism includes, for example, a motor as a driving source and a power transmission mechanism transmitting power of the motor to the table 10. The motor is fixed to the table holding member 11. The power transmission mechanism includes, for example, a driving gear fixed to an output shaft of the motor and a driven gear having a ring shape and a large diameter and fixed to the table 10.

The rolling bearing 12 (hereinafter referred to as a "bearing 12") is a cross roller bearing. The bearing 12 includes a ring-shaped inner race 14 fixed to the table 10, a ring-shaped outer race 15 fixed to the table holding member 11, and a plurality of rollers 16 disposed between the inner race 14 and the outer race 15. The bearing 12 is a relatively large bearing, and the inner race 14 has an inner diameter of, for example, 500 mm. The outer race 15 is composed of two outer race members divided vertically. The two outer race members are fixed to each other with a screw, which is not illustrated. Note that the outer race 15 does not have to be divided into two outer race members. That is, the outer race 15 may be composed of a single member. In this case, the inner race 14 may be composed of two inner race members divided vertically.

The rotation mechanism 7 also includes three or more adjustment members 17 configured to adjust the shape of the outer race 15 by deforming the outer race 15 in assembly of the rotation mechanism 7. The adjustment members 17 of this embodiment are adjusting screws composed of screws. Thus, hereinafter, the adjustment members 17 are referred to as "adjusting screws 17". The rotation mechanism 7 of this embodiment includes, for example, 12 adjusting screws 17. The rotation mechanism 7 also includes looseness preventing screws 18 configured to prevent looseness of the adjusting screws 17. The rotation mechanism 7 includes the same number of the looseness preventing screws 18 as that of the adjusting screws 17. That is, the rotation mechanism 7 includes 12 looseness preventing screws 18.

The table 10 is disposed on the inner circumferential side of the inner race 14. The table 10 is composed of a ring-shaped first table member 19 to which the inner race 14 is fixed and a ring-shaped second table member 20 to which the first table member 19 and the stationary table of the XY table 6 are fixed. X-rays emitted from the X-ray generator 3 pass through the inner circumferential side of the first table member 19 and the second table member 20 formed into ring shapes. The inner race 14 is fixed to the first table member 19 with a fixing screw (not illustrated). The first table member 19 is fixed to the second table member 20 with a fixing screw (not illustrated). The stationary table of the XY table 6 is fixed to the second table member 20 with a fixing screw (not illustrated).

The table holding member 11 is formed into a ring shape. X-rays emitted from the X-ray generator 3 pass through the inner circumferential side of the table holding member 11 formed into the ring shape. On the table holding member 11, a placing surface 11a on which the outer race 15 is placed is formed. The placing surface 11a is formed into a ring shape having the center of curvature being the center of the table holding member 11 formed into the ring shape. Furthermore, the placing surface 11a is a flat surface orthogonal to the vertical direction. The outer race 15 placed on the placing surface 11a is fixed to the table holding member 11 with a plurality of fixing screws 23 arranged in the circumferential direction of the bearing 12.

The outer race 15 is fixed to the table holding member 11 with, for example, 12 fixing screws 23. The 12 fixing screws 23 are arranged at regular pitches in the circumferential direction of the bearing 12. That is, the 12 fixing screws 23 are arranged at pitches of an equal angle (pitches of 30°) relative to the center of the table holding member 11. In the table holding member 11, threaded holes 11b engaging with male threads formed on shanks of the fixing screws 23 are formed. The threaded holes 11b are recessed downward from the placing surface 11a.

In the outer race 15, insertion holes 15a into which the shanks of the fixing screws 23 are inserted are formed. The insertion holes 15a are circular holes passing through the outer race 15 vertically. In this embodiment, to allow deformation of the outer race 15 by the adjusting screws 17, the insertion holes 15a have an inner diameter greater than the outer diameter of the shanks of the fixing screws 23. That is, the insertion holes 15a are so-called clearance holes. The shanks of the fixing screws 23 are inserted into the insertion holes 15a from the upper side of the outer race 15, and heads of the fixing screws 23 are disposed on the upper side of the outer race 15.

On the outer circumferential side of the placing surface 11a of the table holding member 11, a screw holder 11c being an adjustment member holder movably holding the adjusting screws 17 is formed. That is, the table holding member 11 includes the screw holder 11c disposed on the outer circumferential side of the outer race 15. The screw holder 11c is formed into a cylindrical shape protruding upward from the placing surface 11a. Furthermore, the screw holder 11c is formed into a cylindrical shape centered around the center of the table holding member 11. Note that, the screw holder 11c of this embodiment is formed, integrated with a main body of the table holding member 11 on which the placing surface 11a is formed; however, the screw holder 11c formed separately from the main body of the table holding member 11 may be fixed to the main body of the table holding member 11.

In the screw holder 11c, threaded holes 11d engaging with the adjusting screws 17 are formed. In this embodiment, 12 threaded holes 11d are formed in the screw holder 11c. The threaded holes 11d pass through the screw holder 11c in the diameter direction of the screw holder 11c. That is, the threaded holes 11d pass through the screw holder 11c in the diameter direction of the bearing 12. The 12 threaded holes 11d are arranged at regular pitches in the circumferential direction of the bearing 12. That is, the 12 threaded holes 11d are arranged at pitches of an equal angle (pitches of 30°) relative to the center of the table holding member 11. The threaded holes 11d are formed in positions slightly misaligned from the threaded holes 11b in the circumferential direction of the bearing 12 and are formed in the vicinities of the threaded holes 11b in the circumferential direction of the bearing 12.

As illustrated in FIG. 3, between the outer race 15 and the screw holder 11c in the diameter direction of the bearing 12, a gap S configured to allow deformation of the outer race 15 is formed. That is, between an outer circumferential surface of the outer race 15 and an inner circumferential surface of the screw holder 11c in the diameter direction of the bearing 12, the gap S configured to allow deformation of the outer race 15 is formed. The gap S is formed in the entire region in the circumferential direction of the bearing 12. The gap S is, for example, a gap of less than 1 mm.

The adjusting screws 17 are, for example, hexagon socket set screws with no heads. The adjusting screws 17 engage with the threaded holes 11d and are disposed on the outer circumferential side of the outer race 15. The 12 adjusting screws 17 are arranged in the circumferential direction of the bearing 12. Specifically, the 12 adjusting screws 17 are arranged at regular pitches in the circumferential direction of the bearing 12 and are arranged at pitches of an equal angle (pitches of 30°) relative to the center of the table holding member 11. Furthermore, the adjusting screws 17 are movable relative to the screw holder 11c in the diameter direction of the bearing 12. That is, the 12 adjusting screws 17 are disposed radially relative to the center of the table holding member 11. The adjusting screws 17 each have one end contactable with the outer circumferential surface of the outer race 15.

Similar to the adjusting screws 17, the looseness preventing screws 18 are hexagon socket set screws. The looseness preventing screws 18 engage with the threaded holes 11d. Specifically, the looseness preventing screws 18 engage with the threaded holes 11d from outside of the adjusting screws 17 in the diameter direction of the bearing 12. The looseness preventing screws 18 come into contact with the other ends of the adjusting screws 17 with predetermined contact pressure to prevent looseness of the adjusting screws 17.

(Method of Adjusting Rotation Mechanism)

In the X-ray inspection apparatus 1, to bring the rotation locus of the board 2 rotated by the rotation mechanism 7 near to a perfect circle, in assembly of the rotation mechanism 7, the adjusting screws 17 are brought into contact with the outer circumferential surface of the outer race 15 to adjust the shape of the outer race 15, and in that state, the outer race 15 is fixed to the table holding member 11. Specifically, first, a placing stand on which a cylindrical square is placed is fixed to a top surface of the second table member 20, and the cylindrical square is placed on the placing stand. While the table 10 is rotated in that state, displacement of an outer circumferential surface of the cylindrical square is detected with a dial gauge or the like, and the position of the cylindrical square placed on the placing stand is adjusted so that the center of rotation of the table 10 substantially coincides with the axis of the cylindrical square on the basis of a result of the detection of displacement of the outer circumferential surface of the cylindrical square. At this time, the adjusting screws 17 are not in contact with the outer circumferential surface of the outer race 15. Furthermore, the looseness preventing screws 18 are removed.

Then, while the table 10 is rotated, displacement of the outer circumferential surface of the cylindrical square is detected, and the outer race 15 is deformed to adjust the shape of the outer race 15 so that the rotation locus of the cylindrical square is near to a perfect circle on the basis of the detection result of displacement of the outer circumferential surface of the cylindrical square. Specifically, on the basis of the detection result of displacement of the outer circumferential surface of the cylindrical square, the fixing screw 23 closest to a portion of the outer race 15 to be deformed is loosened, and the adjusting screw 17 closest to this fixing screw 23 is turned to move inward in the diameter direction of the bearing 12, so as to be pressed against the outer circumferential surface of the outer race 15. Since the gap S is formed between the outer circumferential surface of the outer race 15 and the inner circumferential surface of the screw holder 11*c*, the outer race 15 deforms in accordance with the amount of rotation of the adjusting screw 17.

Then, after the loosened fixing screw 23 is tightened, displacement of the outer circumferential surface of the cylindrical square is detected again while the table 10 is rotated. Furthermore, on the basis of the detection result of displacement of the outer circumferential surface of the cylindrical square, the fixing screw 23 closest to a portion of the outer race 15 to be deformed is loosened, and the adjusting screw 17 closest to this fixing screw 23 is turned to be pressed against the outer circumferential surface of the outer race 15. Then, the loosened fixing screw 23 is tightened.

These operations are repeated to adjust the shape of the outer race 15 so that the rotation locus of the cylindrical square is near to a perfect circle. When the shape of the outer race 15 is adjusted, the adjusting screw 17 coming into contact with the outer circumferential surface of the outer race 15 may be turned to move outward in the diameter direction of the bearing 12 on the basis of the detection result of displacement of the outer circumferential surface of the cylindrical square. After the shape of the outer race 15 is adjusted, the looseness preventing screws 18 are attached to prevent looseness of the adjusting screws 17. Furthermore, after the shape of the outer race 15 is adjusted, all the fixing screws 23 are tightened firmly, and the outer race 15 is properly fixed to the table holding member 11 with the fixing screws 23.

With the shape of the outer race 15 adjusted so that the rotation locus of the cylindrical square is near to a perfect circle, the rotation locus of the board 2 rotated by the rotation mechanism 7 is also near to a perfect circle. Note that there may be a case where, after the shape of the outer race 15 is adjusted, some adjusting screw 17 are not in contact with the outer circumferential surface of the outer race 15. In this case, before the looseness preventing screws 18 are attached, the adjusting screw 17 that is not in contact with the outer circumferential surface of the outer race 15 is also brought into slight contact with the outer circumferential surface of the outer race 15.

(Main Effects of this Embodiment)

As described above, in this embodiment, the 12 adjusting screws 17 are arranged in the circumferential direction of the bearing 12 and are contactable with the outer circumferential surface of the outer race 15 from the outer circumferential side of the outer race 15. Furthermore, in this embodiment, the gap S configured to allow deformation of the outer race 15 is formed between the outer circumferential surface of the outer race 15 and the inner circumferential surface of the screw holder 11*c*. Thus, in this embodiment, as described above, with the shape of the outer race 15 adjusted using the adjusting screws 17 so that the rotation locus of the board 2 rotated by the rotation mechanism 7 is near to a perfect circle, the outer race 15 can be fixed to the table holding member 11. Therefore, in this embodiment, the rotation locus of the board 2 rotated by the rotation mechanism 7 can be brought near to a perfect circle.

In this embodiment, the shape of the outer race 15 is adjusted with the adjusting screws 17, and the outer race 15 deforms in accordance with the amount of rotation of the adjusting screws 17. Thus, in this embodiment, the shape of the outer race 15 can be readily adjusted. Furthermore, in this embodiment, engagement of the looseness preventing screws 18 with the threaded holes 11*d* engaging with the adjusting screws 17 prevents looseness of the adjusting screws 17, so that a simple configuration can prevent looseness of the adjusting screws 17.

(Modification of Table Holding Member and Rolling Bearing)

Figure 4:
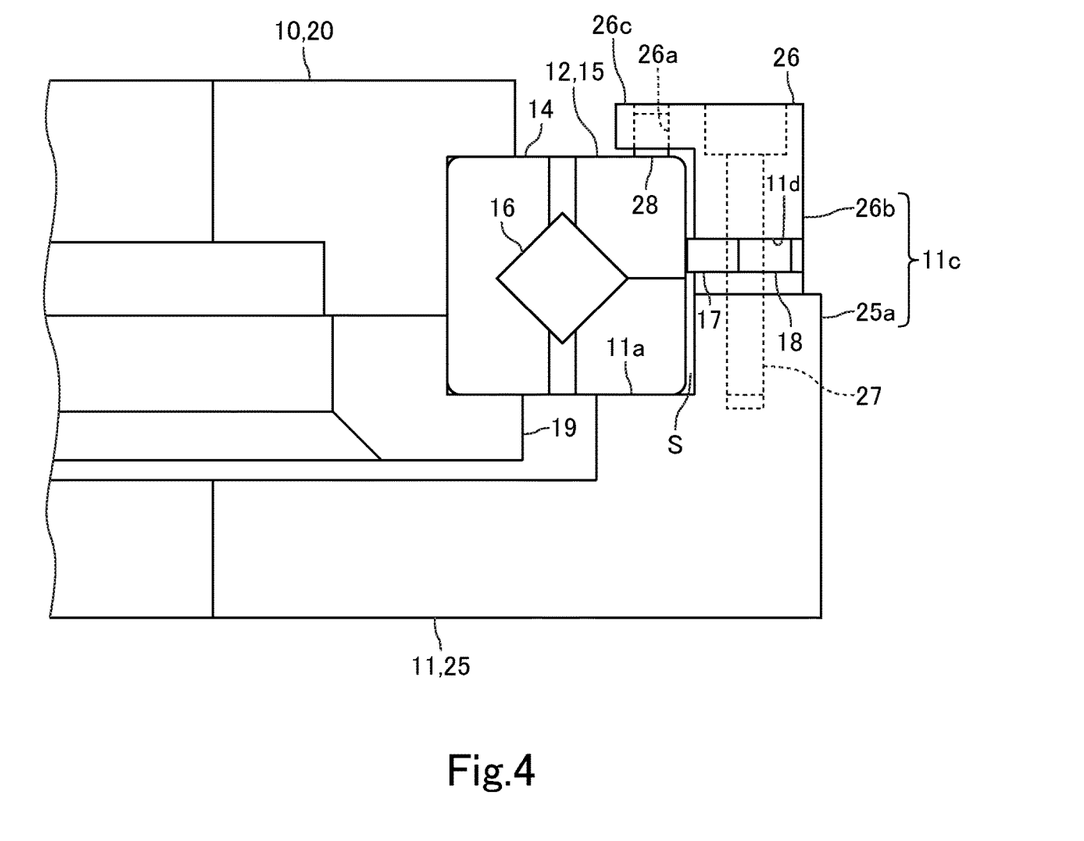
FIG. 4 is an explanatory diagram of a configuration of a table holding member and a rolling bearing according to another embodiment of the present invention.

FIG. 4 is an explanatory diagram of a configuration of the table holding member 11 and the bearing 12 according to another embodiment of the present invention. Note that, in FIG. 4, constituents similar to those in the above-described embodiment are denoted by the same reference signs.

In the above-described embodiment, as illustrated in FIG. 4, the table holding member 11 may be composed of two members, a ring-shaped first holding member 25 and a ring-shaped second holding member 26. In this modification, the placing surface 11*a* is formed on the first holding member 25. On the outer circumferential side of the placing surface 11*a*, a cylindrical portion 25*a* is formed that is shaped into a cylinder and protrudes upward from the placing surface 11*a*. The first holding member 25 and the second holding member 26 are fixed to each other with fixing screws 27. For example, the first holding member 25 and the second holding member 26 are fixed to each other with 12 fixing screws 27 arranged at regular pitches in the circumferential direction of the bearing 12.

In this modification, the outer race 15 is fixed to the table holding member 11 with fixing screws 28 coming into contact with an upper end surface of the outer race 15. Specifically, by pressing the outer race 15 against the placing surface 11*a* with the fixing screws 28, the outer race 15 is fixed to the table holding member 11. The outer race 15 is fixed to the table holding member 11, for example, with 12 fixing screws 28 arranged at regular pitches in the circumferential direction of the bearing 12. The fixing screws 28 are disposed further inward than the fixing screws 27 in the diameter direction of the bearing 12. Furthermore, the fixing screws 28 are disposed, for example, in the same positions as those of the fixing screws 27 in the circumferential direction of the bearing 12. In this modification, no insertion hole 15*a* is formed in the outer race 15, and the outer race 15 has an outer diameter smaller than the outer diameter of the outer race 15 of the above-described embodiment.

The fixing screws 28 are, for example, hexagon socket set screws. In the second holding member 26, threaded holes 26*a* engaging with the fixing screws 28 are formed. In the second holding member 26, the threaded holes 11*d* engaging with the adjusting screws 17 and the looseness preventing screws 18 are also formed. The threaded holes 26*a* are formed in the vicinities of the threaded holes 11*d* in the circumferential direction of the bearing 12. The second holding member 26 is composed of a cylindrical portion 26*b* that is shaped into a cylinder and in which the threaded holes 11*d* are formed and a ring portion 26*c* that is shaped into a ring and in which the threaded holes 26*a* are formed. The ring portion 26*c* protrudes from an upper end portion of the cylindrical portion 26*b* toward the inner circumferential side of the cylindrical portion 26*b*. The cylindrical portion 26*b* has a lower end surface coming into contact with an upper end surface of the cylindrical portion 25a.

In this modification, the cylindrical portion 25a and the cylindrical portion 26b compose the screw holder 11c as the adjustment member holder movably holding the adjusting screws 17 and disposed on the outer circumferential side of the outer race 15. In this modification, the gap S configured to allow deformation of the outer race 15 is also formed between the outer race 15 and the screw holder 11c in the diameter direction of the bearing 12. That is, the gap S configured to allow deformation of the outer race 15 is formed between the outer circumferential surface of the outer race 15 and inner circumferential surfaces of the cylindrical portions 25a and 26b in the diameter direction of the bearing 12. The gap S is formed in the entire region in the circumferential direction of the bearing 12.

In this modification, when the outer race 15 is deformed to adjust the shape of the outer race 15, the fixing screw 28 closest to a portion of the outer race 15 to be deformed is loosened, and the adjusting screw 17 closest to this fixing screw 28 is turned to be pressed against the outer circumferential surface of the outer race 15. Then, the loosened fixing screw 28 is tightened. This modification can also achieve effects similar to those of the above-described embodiment.

Other Embodiments

In the above-described embodiment, the looseness preventing screws 18 may prevent looseness of the adjusting screws 17 by coming into contact with outer circumferential surfaces of the adjusting screws 17 from a direction orthogonal to the axial direction of the adjusting screws 17. In this case, in addition to the threaded holes 11d, threaded holes engaging with the looseness preventing screws 18 are formed in the screw holder 11c. Furthermore, in this case, the adjusting screws 17 may be headed screws having heads. Furthermore, the rotation mechanism 7 may include no looseness preventing screw 18. In this case, for example, looseness of the adjusting screws 17 may be prevented by an adhesive poured into the threaded holes 11d after the shape of the outer race 15 is adjusted.

In the above-described embodiment, the number of the adjusting screws 17 of the rotation mechanism 7 may be 3 or more and 11 or less, or 13 or more. For example, the number of the adjusting screws 17 of the rotation mechanism 7 may be 24. If the number of the adjusting screws 17 of the rotation mechanism 7 is relatively small, the screw holder 11c may not be formed into a cylindrical shape. For example, the screw holder 11c may be an arc-shaped curved plate in which one threaded hole 11d is formed. In this case, a plurality of the screw holders 11c are arranged at regular pitches in the circumferential direction of the bearing 12. Furthermore, in this case, the screw holders 11c may be formed, integrated with the main body of the table holding member 11 on which the placing surface 11a is formed, or the screw holders 11c formed separately from the main body of the table holding member 11 may be fixed to the main body of the table holding member 11.

In the above-described embodiment, insertion holes through which the shanks of the fixing screws 23 are inserted may be formed in the table holding member 11, and threaded holes engaging with the male threads formed on the shanks of the fixing screws 23 may be formed in the outer race 15. Furthermore, in the above-described embodiment, the inner race 14 may be fixed to the table holding member 11, and the outer race 15 may be fixed to the table 10. In this case, the table 10 includes a screw holder corresponding to the screw holder 11c, and in this screw holder, the threaded holes 11d are formed.

In the above-described embodiment, the adjustment members 17 configured to adjust the shape of the outer race 15 by deforming the outer race 15 may be members shaped into rods, tubes, or the like, other than the adjusting screws. For example, the adjustment members 17 may be rods of oil-hydraulic cylinders. In this case, the table holding member 11 includes a cylinder holder to which main bodies of the oil-hydraulic cylinders are fixed. This cylinder holder is an adjustment member holder movably holding the rods of the oil-hydraulic cylinders being the adjustment members 17.

Moreover, in the above-described embodiment, the adjustment member 17 may be eccentric cams. In this case, the table holding member 11 includes a cam holder as an adjustment member holder rotatably holding the eccentric cams. The eccentric cams are movable relative to the cam holder in the diameter direction of the bearing 12. Specifically, outer circumferential surfaces of the eccentric cams are movable relative to the cam holder in the diameter direction of the bearing 12, when viewed vertically.

In the above-described embodiment, as long as the shape of the outer race 15 can be maintained after shape adjustment, the adjusting screws 17 may be removed after the shape of the outer race 15 is adjusted. For example, if the shape of the outer race 15 can be maintained by pouring an adhesive into the gap S after shape adjustment, the adhesive may be poured into the gap S with the shape of the outer race 15 adjusted, and then the adjusting screws 17 may be removed from the threaded holes 11d. That is, the completed rotation mechanism 7 may include no adjusting screw 17.

In the above-described embodiment, the bearing 12 may be a roller bearing or a ball bearing other than a cross roller bearing. Furthermore, in the above-described embodiment, the X-ray inspection apparatus 1 may include no XY table 6. In this case, the placing stand 5 is attached to the rotation mechanism 7. Furthermore, in the above-described embodiment, the object to be inspected with the X-ray inspection apparatus 1 may be an object other than the board 2.

The invention claimed is:

1. A rotation mechanism for an X-ray inspection apparatus used in an X-ray inspection apparatus including an X-ray generator and an X-ray detector disposed with an object to be inspected placed between the X-ray detector and the X-ray generator, the rotation mechanism comprising:
  a table;
  a table holding member rotatably holding the table;
  a rolling bearing including an inner race and an outer race, the inner race having a ring shape and being fixed to either one of the table and the table holding member, the outer race having a ring shape and being fixed to another of the table and the table holding member; and
  three or more adjustment members configured to adjust a shape of the outer race by deforming the outer race, the adjustment members being arranged in a circumferential direction of the rolling bearing,
  the table or the table holding member to which the outer race is fixed including an adjustment member holder movably holding the adjustment members, the adjustment member holder being disposed on an outer circumferential side of the outer race,
  the adjustment members being movable relative to the adjustment member holder in a diameter direction of the rolling bearing and being contactable with an outer circumferential surface of the outer race, and a gap configured to allow deformation of the outer race being formed between the outer circumferential surface of the outer race and the adjustment member holder in the diameter direction of the rolling bearing.

2. The rotation mechanism for an X-ray inspection apparatus according to claim 1, wherein the outer race is fixed to the table holding member.

3. The rotation mechanism for an X-ray inspection apparatus according to claim 1, wherein
the adjustment members are adjusting screws composed of screws, and
threaded holes are formed in the adjustment member holder, the threaded holes engaging with the adjusting screws and passing through the adjustment member holder in the diameter direction of the rolling bearing.

4. The rotation mechanism for an X-ray inspection apparatus according to claim 3, wherein
the rotation mechanism includes looseness preventing screws configured to prevent looseness of the adjusting screws, and
the looseness preventing screws engage with the threaded holes from outside of the adjusting screws in the diameter direction of the rolling bearing.

5. The rotation mechanism for an X-ray inspection apparatus according to claim 1, wherein the rolling bearing is a cross roller bearing.

6. An X-ray inspection apparatus comprising the rotation mechanism for an X-ray inspection apparatus according to claim 1.

7. A method of adjusting a rotation mechanism for an X-ray inspection apparatus used in an X-ray inspection apparatus including an X-ray generator and an X-ray detector disposed with an object to be inspected placed between the X-ray detector and the X-ray generator, the rotation mechanism including a table, a table holding member rotatably holding the table, and a rolling bearing including an inner race and an outer race, the inner race having a ring shape and being fixed to either one of the table and the table holding member, the outer race having a ring shape and being fixed to another of the table and the table holding member, the method comprising:
fixing the outer race to the table or the table holding member with a shape of the outer race adjusted by bringing a plurality of adjustment members into contact with an outer circumferential surface of the outer race, the adjustment members being configured to adjust the shape of the outer race by deforming the outer race, the adjustment members being arranged in a circumferential direction of the rolling bearing.

* * * * *